United States Patent [19]
Totakura et al.

[11] Patent Number: 5,925,065
[45] Date of Patent: Jul. 20, 1999

[54] COATED GUT SUTURE

[75] Inventors: Nagabhushanam Totakura, North Haven; Mark S. Roby, Killingworth, both of Conn.

[73] Assignee: United States Surgical Corporation, Norwalk, Conn.

[21] Appl. No.: 08/744,115

[22] Filed: Nov. 5, 1996

Related U.S. Application Data

[63] Continuation-in-part of application No. 08/657,059, May 28, 1996, abandoned, which is a continuation of application No. 08/338,668, Nov. 14, 1994, abandoned, which is a continuation-in-part of application No. 08/075,995, Jun. 11, 1993, abandoned.

[51] Int. Cl.$^6$ .................................................. A61R 17/00
[52] U.S. Cl. ........................................ 606/229; 606/231
[58] Field of Search ...................... 606/230, 231

[56] References Cited

U.S. PATENT DOCUMENTS

| | | |
|---|---|---|
| 1,239,690 | 9/1917 | Hollister . |
| 2,128,701 | 8/1938 | Gelinsky . |
| 2,394,054 | 2/1946 | Hall . |
| 2,519,404 | 8/1950 | Rynkiewicz . |
| 2,524,772 | 10/1950 | Davis et al. . |
| 2,576,576 | 11/1951 | Cresswell et al. . |
| 2,640,752 | 6/1953 | Davis et al. . |
| 2,694,487 | 11/1954 | Powers et al. . |
| 3,166,073 | 1/1965 | Kronenthal . |
| 3,169,945 | 2/1965 | Hostettler . |
| 3,413,079 | 11/1968 | Rich . |
| 3,478,140 | 11/1969 | Kronenthal et al. . |
| 3,773,737 | 11/1973 | Goodman et al. . |
| 3,896,814 | 7/1975 | Vivien et al. . |
| 3,912,692 | 10/1975 | Casey et al. . |
| 3,942,532 | 3/1976 | Hunter et al. . |
| 4,027,676 | 6/1977 | Mattei . |
| 4,105,034 | 8/1978 | Shalaby et al. . |
| 4,185,637 | 1/1980 | Mattei . |
| 4,190,720 | 2/1980 | Shalaby . |
| 4,201,216 | 5/1980 | Mattei . |
| 4,347,234 | 8/1982 | Wahlig et al. . |
| 4,470,416 | 9/1984 | Kafawy et al. . |
| 4,506,672 | 3/1985 | Bichon . |
| 4,532,929 | 8/1985 | Mattei et al. . |
| 4,605,730 | 8/1986 | Shalaby et al. . |
| 4,624,256 | 11/1986 | Messier et al. . |
| 4,643,191 | 2/1987 | Bezwada et al. . |
| 4,643,734 | 2/1987 | Lin . |
| 4,649,920 | 3/1987 | Rhum . |
| 4,700,704 | 10/1987 | Jamiolkowski et al. . |
| 4,788,979 | 12/1988 | Jarrett et al. . |
| 4,791,929 | 12/1988 | Jarrett et al. . |
| 4,857,602 | 8/1989 | Casey et al. . |
| 4,983,180 | 1/1991 | Kawai et al. . |
| 4,994,074 | 2/1991 | Bezwada et al. . |
| 5,037,429 | 8/1991 | Hermes et al. . |
| 5,037,950 | 8/1991 | Bezwada et al. . |
| 5,076,807 | 12/1991 | Bezwada et al. . |
| 5,080,665 | 1/1992 | Jarrett et al. . |
| 5,085,629 | 2/1992 | Goldberg et al. . |
| 5,100,433 | 3/1992 | Bezwada et al. . |
| 5,104,398 | 4/1992 | Planck et al. . |
| 5,116,932 | 5/1992 | Fujiwa . |
| 5,123,912 | 6/1992 | Kaplan et al. . |
| 5,210,108 | 5/1993 | Spinu et al. . |
| 5,225,521 | 7/1993 | Spinu . |
| 5,278,202 | 1/1994 | Dunn et al. . |
| 5,312,437 | 5/1994 | Hermes et al. . |
| 5,352,515 | 10/1994 | Jarrett et al. . |
| 5,371,176 | 12/1994 | Bezwada et al. . |
| 5,399,666 | 3/1995 | Ford . |
| 5,442,032 | 8/1995 | Arnold et al. . |
| 5,447,966 | 9/1995 | Hermes et al. . |
| 5,530,074 | 6/1996 | Jarrett et al. . |

FOREIGN PATENT DOCUMENTS

| | | |
|---|---|---|
| 0117538 | 9/1984 | European Pat. Off. . |
| 0128043 | 12/1984 | European Pat. Off. . |
| 0628587 | 12/1984 | European Pat. Off. . |
| 8404311 | 11/1984 | WIPO . |

OTHER PUBLICATIONS

Grijpma et al., "Star–shaped polylactide–containing block copolymers", Makromol. Chem., Rapid Commun. vol. 14, pp. 151–161 (1993).

*Primary Examiner*—Michael Buiz
*Assistant Examiner*—William Lewis

[57] ABSTRACT

A coated gut suture is prepared by applying a moisture-retaining substance to the gut suture, followed by coating the suture with a synthetic bioabsorbable polymer. A particularly useful moisture-retaining substance is glycerol. The synthetic bioabsorbable polymer contains a epsilon-caprolactone as the major constituent. The gut suture can be packed in the absence of conventional tubing fluid while retaining flexibility, pliability, and resistance to fray.

7 Claims, No Drawings

COATED GUT SUTURE

RELATED APPLICATIONS

This application is a continuation-in-part of U.S. application Ser. No. 08/657,059 filed May 28, 1996, now abandoned which is a continuation of U.S. application Ser. No. 08/338,668 filed Nov. 14, 1994, now abandoned, which is a continuation-in-part of U.S. application Ser. No. 08/075,995 filed Jun. 11, 1993, now abandoned.

BACKGROUND

1. Technical Field

A coated gut suture and, more particularly, a coated gut suture which is capable of being dry packaged is disclosed.

2. Background of the Related Art

Absorbable sutures are manufactured from natural or synthetic materials. Some of the earliest absorbable sutures were made of collagenous material taken from sheep intestines. Such sutures are still in use today and are commonly referred to as "catgut" or simply "gut" sutures or ligatures. As used herein, the term "catgut" or "gut" suture refers to a collagen based suture or ligature of any type or origin. Gut sutures may be prepared in the form of threads or strands that are undesirably stiff before subsequent treatment which renders them flexible or pliable.

A suture having a good degree of flexibility and pliability can conform closely to body tissue without undue pressure. Good flexibility and pliability enhance the degree to which a suture can be tied down, knotted and securely placed in a desired position. "Fray resistance" refers to the ability of the suture to resist fraying when rubbing against itself as, for example, when a knot is run down the suture. When knots are run down a suture, the knot run down should be smooth, with a minimum of "chatter" or frictional vibration.

Various attempts have been made to modify and optimize the physical characteristics of gut sutures. For example, tubing fluids, i.e., liquids which are used to condition gut sutures to achieve or enhance flexibility and pliability, have been used to preserve gut sutures. Tubing fluids typically contain an alcohol such as isopropyl alcohol and water. In the tubing fluid, the gut suture retains its flexibility and pliability.

In addition to tubing fluids, various suture coatings have been developed in an attempt to maintain flexibility and control swelling and fraying. Such coatings are also intended to improve the handling characteristics of sutures and maximize run-down performance. Commercially available gut sutures are immersed in tubing fluid, sterilized and supplied to surgeons in packages or tubes which contain tubing fluid. The suture remains flexible and pliable as long as it remains in contact with the tubing fluid. However, the gut sutures are wet when removed from the package and tubing fluid can spill out of the package if not handled properly.

It would be desirable to provide a gut suture that exhibits good flexibility and pliability, high fray resistance and which does not chatter when knots are run down the suture. It would also be desirable if a suture possessing the above-mentioned physical characteristics could be packaged dry, without the need for tubing fluid.

SUMMARY

Novel coated gut sutures and methods for their production are provided herein. The suture is a collagenous strand that is treated with a moisture-retaining substance such as, for example, glycerol and then coated with a synthetic bioabsorbable polymer. Particularly useful synthetic bioabsorbable polymers contain caprolactone linkages. The resulting gut suture exhibits excellent handling characteristics, including good fray resistance and can be packaged with or without tubing fluid.

The method includes treating at least one strand of collagenous material with an aqueous solution of a moisture-retaining substance, and coating the treated strand with a synthetic bioabsorbable polymer, such as for example, copolymers containing a major amount of caprolactone units and a minor amount of another bioabsorbable constituent such as glycolide, lactide, dioxanone, or trimethylene carbonate. After being coated, the suture can be dried at an elevated temperature in flowing nitrogen or in a vacuum. Therapeutic agents may be incorporated into the bioabsorbable polymer.

DETAILED DESCRIPTION OF PREFERRED EMBODIMENTS

In the embodiments described herein a gut suture is treated with a moisture-retaining substance and then coated with a polymer including caprolactone linkages, and then dried. The resulting suture exhibits superior fray resistance and knot run down characteristics even when stored in the dry condition.

Another advantage of the coated gut suture prepared by the method described herein is that it can be sterilized by a variety of dry sterilization methods, such as chemical sterilization (e.g., exposure to ethylene oxide), or by gamma irradiation (e.g., exposure to a cobalt-60 gamma source).

The gut sutures used herein, which can be of any size and either chromacized or plain gut, are prepared in a conventional manner. By way of illustration, beef serosa ribbons are desalinated and assembled. They are then soaked in wet phase treatment in baths of sodium carbonate, hydrogen peroxide, and water. Plain catguts are then soaked in sodium hydrosulfite and then soft water, whereas chromic catguts are then soaked in pyrogallic acid, sodium bichromate to which sodium bisulfite is later added, and optionally gelatin. After the wet phase treatments the wet catguts are then twisted. This operation blends the serosa lengths before the drying operation which creates chemical liaisons between the collagen molecules. After twisting the catguts are dried and cut to final length. The catguts are then machine polished. Chromic catguts are further soaked in an aqueous solution of ethanol and glycerine.

The gut sutures are first treated by dipping into a aqueous solution of a moisture-retaining substance. The sutures can be individually dipped, or tied end to end and run over rollers into trays of dipping solution in a continuous process. Alternatively any other suitable processes for applying a liquid may optionally be used, for example, conducting the suture past a brush or other applicator, or passing the suture through a spray or mist.

Suitable materials capable of retaining moisture in the gut suture include, for example, substances having by humectant or hygroscopic properties. Suitable substances include triethyl citrate, glycerol, ethylene glycol, propylene glycol, and/or other polyhydric alcohols, fatty acids, fatty alcohols, esters and ethers of fatty acids, and poly(alkylene oxides). Glycerol is a particularly useful moisture-retaining substance. The concentration of moisture-retaining substance in the dipping solution can be from about 1% to about 99% by weight of the solution, more preferably from about 5% to about 50% and most preferably from about 20% to about 30%. The temperature of the dipping solution can optionally be heated to a temperature up to about 90° C., preferably from about 30° C. to about 80° C., and more preferably from about 40° C. to about 60° C. The duration of dipping time can be any time sufficient to apply a coating of the solution onto the suture. For example, preferred dipping times can range from 1 minute to 48 hours, more preferably from about 5 minutes to 6 hours, and most preferably from about 10 minutes to 1 hour.

After the suture has been removed from the dipping solution the excess solution is drained off for about 1 to 10 minutes, preferably 2 to 5 minutes. The suture is then optionally immersed in a low molecular weight alcohol, e.g. ethanol or isopropanol, for about 5 to 15 seconds, preferably about 10 seconds, to remove residual water. Alternatively, if the time for draining the dipping solution is long enough, the alcohol dip can be avoided. If the alcohol dip is employed a period of time is allotted to drain off the alcohol. This time ranges from about 1 to about 5 minutes, preferably about 2 minutes.

Next, the sutures are dipped in coating solution, which contains a synthetic bioabsorbable polymer. Particularly useful synthetic bioabsorbable polymers contain caprolactone linkages. The polymer can be caprolactone homopolymer, a blend of polymers which contains as one component a polymer including a major amount (i.e., more than 50 mole percent) of caprolactone linkages, or a copolymer with caprolactone units as the major constituent (i.e., more than 50 mole percent) and one or more minor constituents.

Conventional polymerization techniques that are well known and disclosed in the prior art can be utilized in preparing the preferred bioabsorbable copolymer employed as a coating composition for a gut suture. Preferably, the bioabsorbable copolymer is obtained by polymerizing a major amount of epsilon-caprolactone and a minor amount of at least one other copolymerizable bioabsorbable monomer or mixture of such monomers. Suitable bioabsorbable monomers which can be copolymerized with epsilon-caprolactone include glycolide, lactide, p-dioxanone and trimethylene carbonate.

Polymerization may optionally be performed in the presence of a polyhydric alcohol initiator such as glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like. The polymerization contemplates all of the various types of monomer addition, i.e., simultaneous, sequential, simultaneous followed by sequential, sequential followed by simultaneous, etc.

The copolymer can contain from about 70% to about 98%, and preferably from about 80% to about 95%, epsilon-caprolactone-derived units, the balance of the copolymer being derived from the other copolymerizable monomer(s). The inherent viscosity of the copolymer generally ranges from about 0.10 to about 0.60, and preferably from about 0.20 to about 0.50, dl/g when measured in chloroform at a concentration of 0.25 g/dl at 30° C. If used, the polyhydric alcohol initiator is generally employed in small amounts, e.g., from about 0.5 to about 5, and preferably from about 0.1 to about 2, weight percent of the total monomer mixture.

The bioabsorbable copolymer can be applied to a gut suture by any suitable process, e.g., by passing the gut suture through a solution of the copolymer in, e.g., acetone, methylene chloride, methyl ethyl ketone (MEK), xylene, toluene, or past a brush or other coating solution applicator, or past one or more spray nozzles dispensing the gut suture coating solution. The percentage of polymer in the coating solution can range from, for example, about 0.5% to about 10%, and preferably from about 3% to 5%, by weight. Preferably, the suture is dipped in the solution of polymer coating agent for a period of time ranging from about 5 seconds to about one minute. The gut suture wetted with the coating solution is subsequently dried in air, flowing nitrogen, or in a vacuum and/or passed through or held in a drying oven for a time and at a temperature sufficient to vaporize and drive off the solvent. Preferably, the coated gut suture is first drained and then dried in an oven maintained at a temperature of from about 30° C. to about 60° C., and more preferably about 50° C. for a period of time ranging from about 15 minutes to 3 hours. The bioabsorbable copolymer will entrap moisture within the suture and/or enhance the retention of the moisture within the suture.

If desired, the gut suture coating composition can optionally contain additional components, e.g., dyes, and or therapeutic agents such as antibiotics, antiseptics, growth factors, anti-inflammatory agents, etc. The amount of coating composition applied to a gut suture will vary depending upon the structure of the suture, e.g., the number of filaments, tightness of braid or twist, the size of the suture and its composition.

After oven drying, the suture is stored in a dry room for about one hour and is allowed to reach equilibrium with ambient temperature.

The suture may then be cut and stored. Alternative storage methods are to pack the gut suture dry in sealed foil packets, or to store the gut suture in tubing fluid. A suitable tubing fluid includes about 9% to about 12% water, about 1% to about 2% triethanolamine, and about 86% to 90% isopropyl alcohol.

The resulting coated gut sutures can generally contain from about 0.1% to about 15% or more of the moisture-retaining substance (e.g., glycerol) and from about 0.5% to about 5% polymer based on the final weight of the coated gut suture. As a practical matter, it is generally preferred to apply the minimum amount of coating composition consistent with good handling, fray resistance, and run-down performance. This level of coating can be readily determined using routine experimental procedure.

The following examples should be considered as illustrative and not as limitations of the present description. The examples demonstrate that coating formulations containing bioabsorbable copolymer and pre-coating composition as disclosed herein enhance the properties of gut sutures coated therewith.

EXAMPLE 1

A glycerol solution is prepared by mixing 30 grams of glycerol with 70 grams of pyrogen free water. The solution is stirred for 5 minutes at room temperature.

A 5% solution of polymer coating material is prepared by dissolving 5 grams of a copolymer comprising 90% epsilon-caprolactone/10% glycolide in 100 grams of toluene, with stirring for 2 hours.

The aqueous glycerol solution is heated to 50° C. Thirty strands of 60" chrome gut sutures (size 1) are coiled and dipped into the glycerol solution at 50° C. and allowed to soak for 10 minutes.

After being removed from the glycerol solution and allowed to drain for about 5 minutes the sutures are dipped into isopropyl alcohol for about 10 seconds. The sutures are removed from the isopropyl alcohol and allowed to drain for about 2 minutes. The sutures are then dipped in the polymer coating solution for about 15 seconds, removed from the solution and allowed to drain for about 30 seconds.

The sutures are dried under a nitrogen flow of 5 cubic feet per minute in an oven at about 50° C. for about 30 minutes.

The dried sutures are divided into two batches: 1A and 1B. Batch 1A is packed dry in aluminum foil. Batch 1B is stored in a tubing fluid containing 9 grams of pyrogen free water, 1.4 grams of triethanolamine and 89.6 grams of isopropyl alcohol. The sutures are allowed to stay in the tubing fluid for at least 4 hours before testing.

Table top knot run down tests for this Example and the following Examples are manually performed by tying overhand knots in the suture, running the knots down the suture being tested, and visually observing whether fraying occurred.

The sutures of both batches 1A and 1B are very smooth, even after storage. Also, more than 15 knots can be run down the sutures of each of the batches without fraying.

EXAMPLE 2

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% epsilon-caprolactone/10% glycolide in 100 cc of methyl ethyl ketone.

Fifty strands of 60" size 1 chrome gut sutures are dipped in the aqueous glycerol solution and allowed to soak at room temperature for 24 hours. The sutures are removed from the glycerol solution and allowed to drain for about 5 minutes.

The sutures are then dipped in isopropyl alcohol for 10 seconds, removed therefrom and allowed to drain for about 2 minutes. The sutures are then dipped in the polymer coating solution for 15 seconds at room temperature, removed from the polymer coating solution and allowed to drain for 30 seconds. The treated sutures are then divided into 4 batches: 2A, 2B, 2C, 2D.

Batch 2A is dried under full vacuum without heat for 1 hour and is packaged dry in aluminum foil. Upon performance of the manual test for fray resistance these sutures exhibit fraying after 7 knot run downs.

Batch 2B is dried in a nitrogen flow oven at a flow rate of 5 cubic feet per minute for 30 minutes at 30° C. Upon performance of the manual test for fray resistance these sutures exhibit fraying after 8 knot run downs.

Batch 2C is dried in a nitrogen flow oven at a flow rate of 5 cubic feet per minute for 30 minutes at 40° C. Upon performance of the manual test for fray resistance these sutures exhibit fraying after 7 knot run downs.

Batch 2D is dried in a nitrogen flow oven at a flow rate of 5 cubic feet per minute for 30 minutes at 45° C. Upon performance of the manual test for fray resistance these sutures exhibit fraying after 15 knot run downs.

EXAMPLE 3

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% epsilon-caprolactone/10% glycolide in 100 cc of methyl ethyl ketone.

Fifty strands of 60" size 1 chrome gut sutures are tied together at both ends and dipped as a bundle in the aqueous glycerol solution and allowed to soak at room temperature for 6 hours. After being removed from the glycerol solution and allowed to drain for about 5 minutes the sutures are dipped in isopropyl alcohol for 10 seconds. The sutures are removed from the isopropyl alcohol solution, and allowed to drain for about 2 minutes.

The sutures are then dipped in the polymer coating solution for 15 seconds at room temperature, removed from this solution, and allowed to drain for 30 seconds. These sutures are then divided into two batches: 3A and 3B.

Batch 3A is dried in a nitrogen flow oven at 5 cubic feet per minute flow rate and 50° C. for 10 minutes. The sutures are then packed dry. When removed for testing the sutures are sticky and have imperfections. However, upon performance of the manual test for fray resistance the sutures do not fray even after 15 knot run downs.

Batch 3B is dried under vacuum at 30° C. for 5 minutes. The resulting sutures have imperfections. However, upon performance of the manual test for fray resistance the sutures do not fray even after 15 knot run downs.

EXAMPLE 4

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% epsilon-caprolactone/10% glycolide in 100 cc of methyl ethyl ketone.

Fifty strands of 60" size 1 chrome gut sutures are tied together at both ends and dipped as bundle in the aqueous glycerol solution and allowed to soak at room temperature for 1 hour. After being removed from the glycerol solution and allowed to drain for about 5 minutes the sutures are dipped in isopropyl alcohol for 10 seconds, removed from the isopropyl alcohol solution, and allowed to drain for about 2 minutes.

The sutures are then dipped in the polymer coating solution for 15 seconds at room temperature, removed from this solution and allowed to drain for 30 seconds. These sutures are divided into two batches: 4A and 4B.

Batch 4A is dried in a nitrogen flow oven at 5 cubic feet per minute flow rate and 50° C. for 15 minutes. The sutures were then packed dry. When removed for testing the sutures had no imperfections. Upon performance of the manual test for fray resistance the sutures do not fray even after 15 knot run downs.

Batch 3B is dried under vacuum at 45° C. for 15 minutes. The resulting sutures have imperfections. However, upon performance of the manual test for fray resistance the sutures do not fray even after 15 knot run downs.

EXAMPLE 5

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% epsilon-caprolactone/10% glycolide in 100 cc of methyl ethyl ketone.

Fifty strands of 60" size 1 chrome gut sutures are tied together at both ends and dipped as a bundle in the aqueous glycerol solution and allowed to soak at room temperature for 1 hour. After being removed from the glycerol solution and allowed to drain for about 5 minutes the sutures are dipped in isopropyl alcohol for 10 seconds, removed from the isopropyl alcohol solution, and allowed to drain for about 2 minutes.

The sutures are then dipped in the polymer coating solution for 15 seconds at room temperature, removed from this solution and allowed to drain for 30 seconds.

These sutures are then dried in a nitrogen flow oven with a 5 cubic feet per minute flow rate at 50° C. for 30 minutes. The resulting sutures had a good appearance with no visible imperfections. Upon performance of the manual test for fray resistance the sutures do not fray even after 15 knot run downs.

EXAMPLE 6

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% epsilon-caprolactone/10% glycolide in 100 cc of methyl ethyl ketone.

Fifty strands of 60" size 1 chrome gut sutures are tied together at both ends and dipped as a bundle in the aqueous glycerol solution and allowed to soak at room temperature for 30 minutes. After being removed from the glycerol solution and allowed to drain for about 5 minutes the sutures are dipped in isopropyl alcohol for 10 seconds, removed from the isopropyl alcohol solution, and allowed to drain for about 2 minutes.

The sutures are then dipped in the polymer coating solution for 15 seconds at room temperature, removed from this solution and allowed to drain for 30 seconds.

These sutures are then dried in a nitrogen flow oven with 5 cubic feet per minute flow rate at 50° C. for 30 minutes. The resulting sutures have a good appearance with no visible imperfections. Upon performance of the manual test for fray resistance the sutures do not fray even after 15 knot run downs.

EXAMPLE 7

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% E-caprolactone/10% glycolide in 100 cc of methyl ethyl ketone.

Three hundred strands of 35" size 1 chrome gut sutures are tied together at both ends and dipped as bundles in the aqueous glycerol solution and allowed to soak at room temperature for 1 hour. After being removed from the glycerol solution and allowed to drain for about 5 minutes the sutures are dipped in isopropyl alcohol for 10 seconds, removed from the isopropyl alcohol solution, and allowed to drain for about 2 minutes.

The sutures are then dipped in the polymer coating solution for 30 seconds at room temperature, removed from this solution and allowed to drain for 30 seconds.

These sutures are then dried in a nitrogen flow oven with a 5 cubic feet per minute flow rate at 50° C. for 30 minutes. The sutures are thereafter allowed to reach ambient temperature in a dry room and are then packaged dry in aluminum foil.

The resulting sutures have a good appearance with no visible imperfections. Upon performance of the manual test for fray resistance the sutures do not fray even after 15 knot run downs.

EXAMPLE 8

An aqueous glycerol solution is prepared by mixing 20 grams of glycerol with 80 grams of pyrogen-free water. The solution is stirred for 5 minutes at room temperature.

A 5% solution of coating material is made by dissolving 5 grams of a copolymer comprising 90% epsilon-caprolactone/10% glycolide in 100 cc of methyl ethyl ketone.

Two hundred strands of 30" size 1 plain gut sutures are tied together at both ends and dipped as bundles in the aqueous glycerol solution and allowed to soak at room temperature for 1 hour. After being removed from the glycerol solution and allowed to drain for about 5 minutes the sutures are dipped in isopropyl alcohol for 10 seconds, removed from the isopropyl alcohol solution, and allowed to drain for about 2 minutes.

The sutures are dipped in the polymer coating solution for 30 seconds at room temperature, removed from this solution and allowed to drain for 30 seconds.

These sutures are then dried in a nitrogen flow oven with a 5 cubic feet per minute flow rate at 50° C. for 30 minutes. The sutures are thereafter allowed to reach ambient temperature in a dry room and are then packaged dry in aluminum foil.

The resulting sutures have a good appearance with no visible imperfections. Upon performance of the manual test for fray resistance the sutures do not fray even after 15 knot run downs.

COMPARATIVE EXAMPLE A

Fifty strands of 60" size 1 chrome gut sutures are provided. These are divided into two batches: A-1 and A-2.

Batch A-1 is stored dry in aluminum foil. Upon performance of the manual test for fray resistance the sutures fray immediately upon the first knot run down.

Batch A-2 is stored in tubing fluid containing 9 grams of pyrogen free water, 1.4 grams of triethanolamine, and 89.6 grams of isopropyl alcohol. The sutures are allowed to stay in the tubing fluid for at least 4 hours before testing. Upon performance of the manual test for fray resistance these sutures exhibit fraying after about 3 knot run downs.

The Examples set forth above illustrate the effectiveness of the coating method described herein in preserving and/or improving handling characteristics for gut sutures, even if the gut sutures are stored in dry condition.

It will be understood that various modifications may be made to the embodiments disclosed herein. Therefore, the above descriptions should not be construed as limiting, but merely as exemplifications of preferred embodiments. Those skilled in the art will envision other modifications within the scope and spirit of the claims applied hereto.

What is claimed is:

1. A surgical suture comprising:
    a) a strand of collagenous material treated with a moisture-retaining substance; and (b) a synthetic bioabsorbable polymer coating on the treated strand.

2. The surgical suture of claim 1 wherein the moisture-retaining substance is a material selected from the group consisting of polyhydric alcohols, fatty acid alcohols, fatty acid esters, fatty acid ethers, poly (alkylene oxides), and triethyl citrate.

3. The surgical suture of claim 1 wherein the moisture-retaining substance is glycerol.

4. The surgical suture of claim 1 wherein the synthetic bioabsorbable polymer contains units of epsilon-caprolactone.

5. The surgical suture of claim 1 wherein the synthetic bioabsorbable polymer is a copolymer of a major amount of epsilon-caprolactone and a minor amount of monomer units selected from the group consisting of glycolide, lactide, p-dioxanone, and trimethylene carbonate.

6. The surgical suture of claim 1 wherein the moisture-retaining substance is glycerol and the synthetic bioabsorbable coating comprises a copolymer of about 10% glycolide units and 90% epsilon-caprolactone units.

7. A gut suture comprising a strand of collagenous material having a coating of a synthetic bioabsorbable polymer, the suture exhibiting no visible fraying after more than about 5 overhand knots are run down the suture.

* * * * *